United States Patent [19]

Spector

[11] Patent Number: 4,747,539

[45] Date of Patent: May 31, 1988

[54] REVERSIBLE ON-OFF FRAGRANCE EMITTING UNIT

[76] Inventor: Donald Spector, 380 Mountain Rd., Union City, N.J. 07087

[21] Appl. No.: 49,855

[22] Filed: May 15, 1987

[51] Int. Cl.$^4$ .............................................. A61L 9/04
[52] U.S. Cl. ...................................... 239/56; 239/45; 239/47
[58] Field of Search ...................... 220/93; 239/45, 47, 239/53, 55, 44, 60; 422/122, 123

[56] References Cited

U.S. PATENT DOCUMENTS

| | | | |
|---|---|---|---|
| 2,120,204 | 6/1938 | Langhorst | 239/54 |
| 4,149,675 | 4/1979 | Van Breen et al. | 239/55 X |
| 4,226,829 | 10/1980 | Mike | 239/55 X |

Primary Examiner—Andres Kashnikow
Assistant Examiner—Kevin Patrick Weldon
Attorney, Agent, or Firm—Michael Ebert

[57] ABSTRACT

A reversible fragrance emitting unit adapted to rest on a flat surface in either an upright or an upside down position, no fragrance being emitted in one position and fragrance being emitted in the other position, so that a switching action is effected simply by reversing the unit. The unit consists of a vented cylindrical shell closed at its upper end by a cover plate and at its lower end by a bottom wall. Disposed within the shell and secured to the cover plate is an absorbent pad. Joined to the pad is the leading end of a series of interhinged absorbent elements in an accordian formation, the trailing end of the series being joined to a weight whereby when the unit is upside down, the accordian is collapsed on the bottom wall and compressed by the overlying weight, and when the unit is reversed in position and is made upright, the weight drops to the bottom wall, thereby expanding the accordian. The pad and the elements of the accordian are impregnated with a volatile fragrance, the pad acting as a reservoir therefor, whereby in the upside down position of the unit when the accordian is collapsed, no fragrance is emitted, and when in the upright position in which the accordian is expanded to expose the elements thereof, fragrance is emitted.

7 Claims, 2 Drawing Sheets

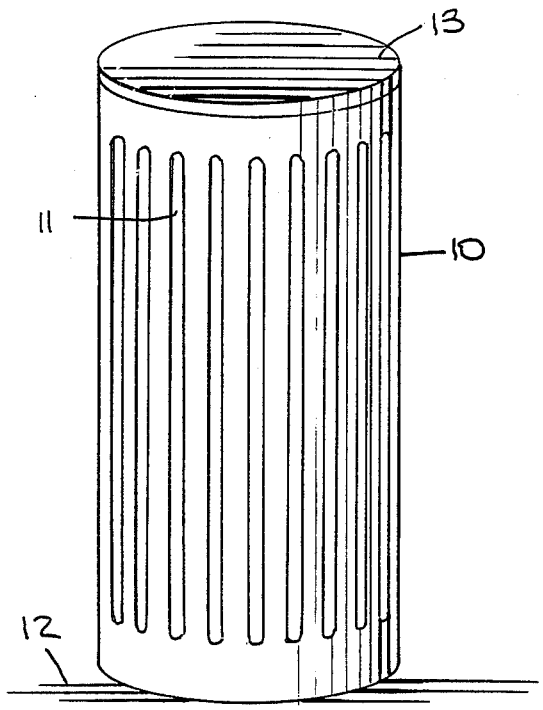
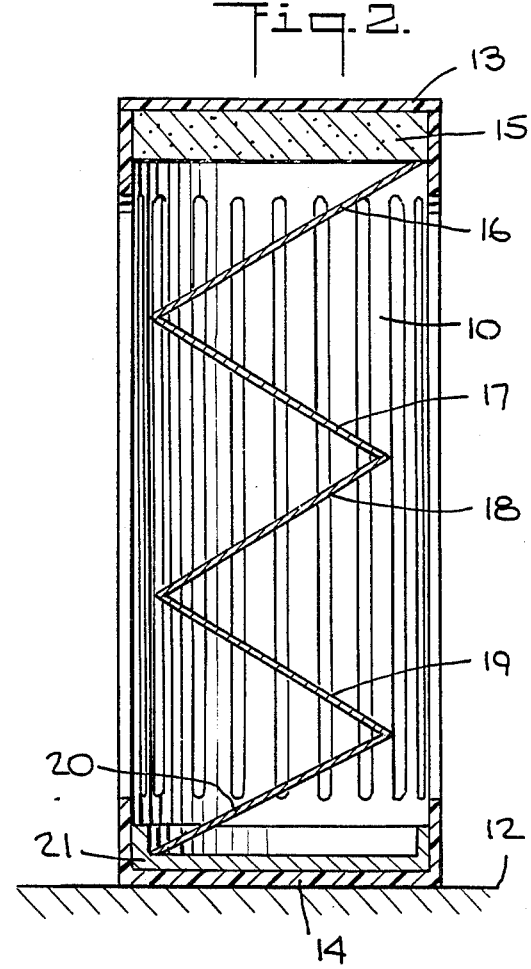
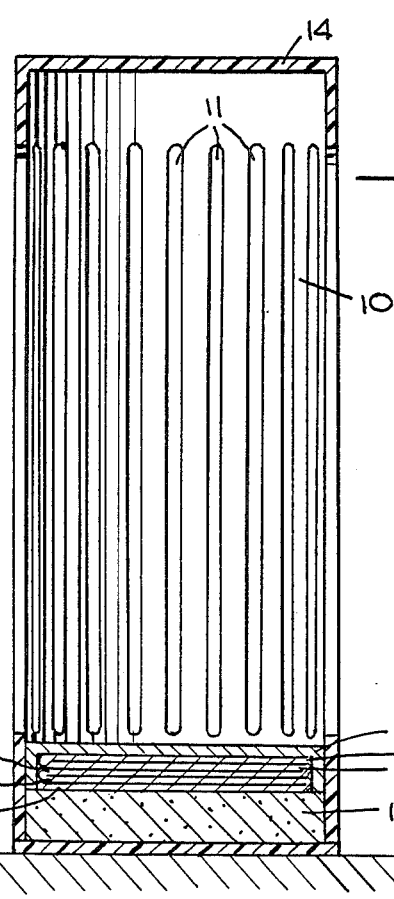
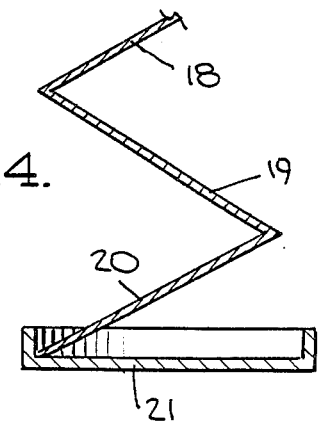

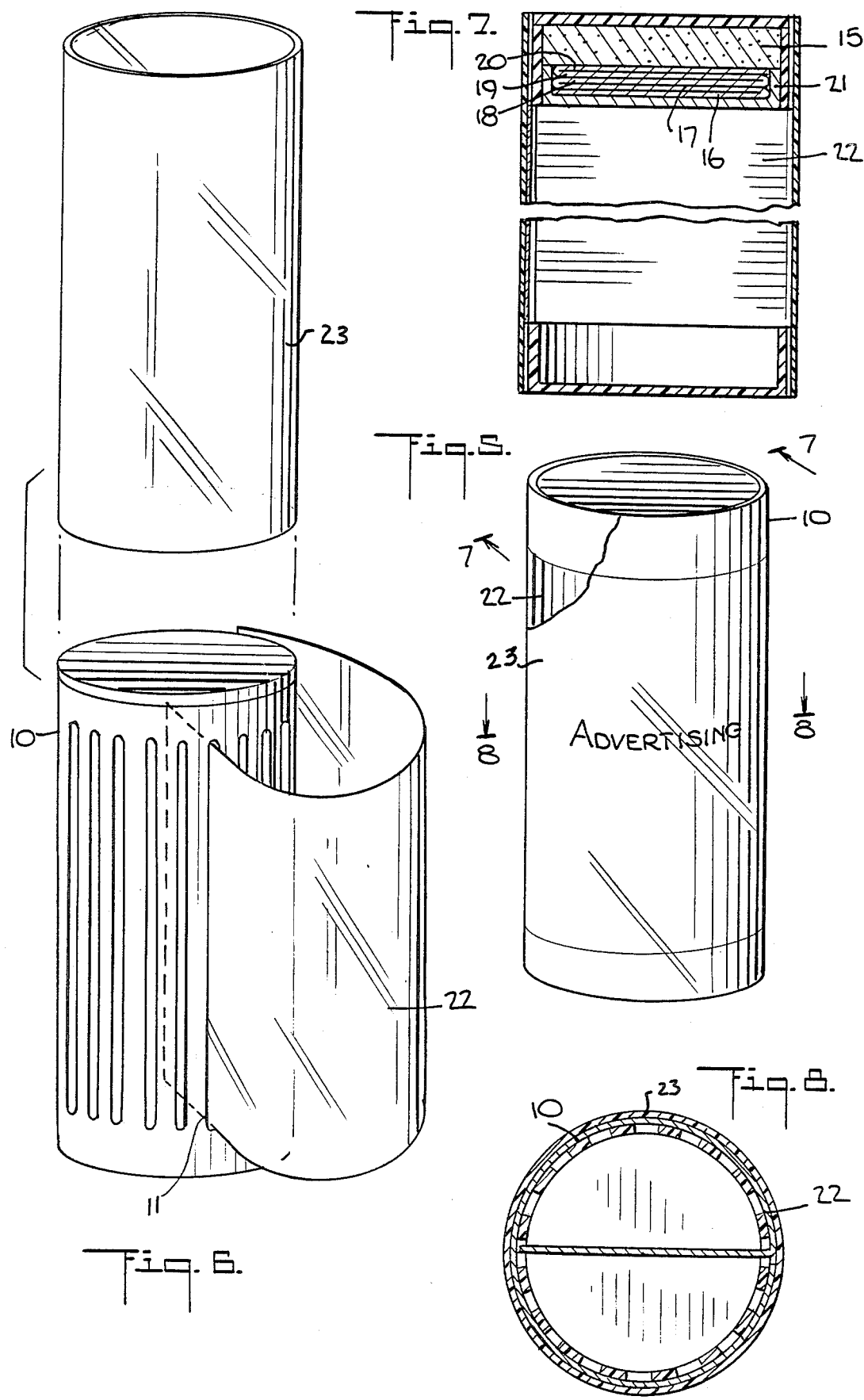

REVERSIBLE ON-OFF FRAGRANCE EMITTING UNIT

BACKGROUND OF INVENTION

1. Field of Invention

This invention relates generally to environmental aroma generators functioning to exude a fragrance into the atmosphere of a room, and more particularly to a reversible fragrance-emitting unit adapted to rest on a table or other flat surface in either an upright position in which substantially no fragrance is emitted or in an upside down position in which fragrance is emitted. Hence to turn the unit "off," one has simply to place it in its upright position.

2. Status of Prior Art

As used herein, the term "aroma" or "fragrance" is not limited to pleasant or savory smells but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

There are many situations in which the environment of a living room, a kitchen, an office or other enclosure occupied by people is rendered unpleasant by tobacco smoke, food smells or other pungent odors. It is often not practical, as in the winter months, to open a window or operate an air conditioner to clear the air. The common practice, therefore, is to mask or modify the prevailing atmosphere by some sort of air freshener device or aroma generator.

In some situations, the atmosphere of a room may be clear and free of odors, yet it may be desirable to introduce a fragrance in order to create a more romantic ambience or to induce other effects, for personal moods are highly influenced by odors. Thus, the effect of a musk-like odor is very different from that of sea air and such differences can be exploited when manipulating the environment.

It is known to provide an air freshener or fragrance generator in the form of a bottle containing a volatile liquid in which a wick is immersed, the upper end of the wick extending above the bottle and being exposed to the air. Such devices not only are subject to spillage or leakage, but, in order to adjust the rate of volatilization, means must be provided to vary the extent of wick exposure.

The patent to Meek, U.S. Pat. No. 2,763,395, discloses an air freshener in which a vented cylindrical container is filled with particles or absorbent material impregnated with a volatile air-freshener liquid. The vented container is telescoped within a cylindrical housing and is provided with detents making it possible to more or less raise the vented container relative to its housing and thereby more or less expose the impregnated particles to the atmosphere. In this way, one can adjust the rate of odor or air freshener dissemination. A vapor dispenser having telescoping elements to adjust the rate of dissemination is also shown in the Martens et al. U.S. Pat. No. 4,220,281.

In the Munnecke U.S. Pat. No. 2,578,827, a deodorizer is disclosed in which an absorbent filler held in a container is impregnated with a volatile liquid. In this unit, the rate of emission is controlled by an adjustable shutter in which two sets of holes are more or less brought into registration with each other.

Apart from the mechanical complexity of the units disclosed in the above-identified patents is the fact that that they have an appearance that is strictly utilitarian and devoid of aesthetic appeal. The functional character of these units is not objectionable when they are installed in a workplace or kitchen. But in a living room or in other well-appointed enclosures, odor emitting units of the prior art type strike a discordant note, and they are usually not acceptable. Where one wishes to conceal the source of scent emission and give the impression that the atmosphere is naturally agreeable, this purpose is not served by prior art forms of aroma generators whose true function is undisguised.

My prior U.S. Pat. No. 4,612,223 discloses a fragrance emitting unit having a pleasing decorative appearance which renders it acceptable in a well-appointed room or other enclosure, the rate of fragrance emission being adjustable from an almost "off" to a full "on" rate without the need for mechanical expedients.

The unit disclosed in my prior patent consists of a fenestrated open-ended shell in an hourglass formation whose inlet and outlet ends are attached to inlet and outlet boxes of like dimensions, both having bottom walls. The inlet box has an open top, whereas the outlet box is closed by a top wall to define an internal chamber which extends through the shell between the bottom wall of the inlet box and the top wall of the outlet box. The chamber contains a charge of fragrance-emitting pellets in an amount sufficient to almost fill the inlet box when the unit is placed in its upright position in which the inlet box rests on the table and the pellets are confined within the inlet box and therefore emit relatively little fragrance, the unit being effectively "off." When, however, the unit is reversed to occupy its upside down position in which the outlet box rests on the table, the pallets then occupy the shell and emit fragrance through the openings therein at a much greater rate and the unit is "on."

From the commercial standpoint, the unit disclosed in my prior patent has certain practical drawbacks, for it requires the use of aromatic pellets impregnated with a volatile liquid fragrance. These are relatively expensive to make. Another objection is that this unit has a relatively complex structure, for it requires an inlet and an outlet box at the ends of the openended shell.

Also of prior art interest are the following U.S. patents:

U.S. Pat. No. 2,414,902, 1/1947 Schlumboln
U.S. Pat. No. 2,766,067, 10/1956, Shinberg
U.S. Pat. No. 2,982,458, 5/1961, Hennion
U.S. Pat. No. 4,069,996, 1/1978, Koziol
U.S. Pat. No. 4,149,675, 4/1979, Van Breen et al.
U.S. Pat. No. 4,220,281, 9/1980, Martens, III et al.
U.S. Pat. No. 4,226,829, 10/1980, Mike
U.S. Pat. No. 4,346,840, 8/1982, Gaiser et al.
U.S. Pat. No. 4,436,203, 3/1984, Reyner
U.S. Pat. No. 4,523,870, 6/1985, Spector
U.S. Pat. No. 4,537,351, 8/1985, Wilson

SUMMARY OF INVENTION

In view of the foregoing, the main object of this invention is to provide a reversible fragrance emitting ON-OFF unit having a pleasing decorative appearance which renders it acceptable in a well-appointed room or other enclosure.

More particularly, an object of this invention is to provide a reversible unit of the above type which is adapted to rest on a table or other flat surface in either an upright position in which the unit effectively is OFF or in an upside down position in which the unit is ON, the appearance of the unit being about the same in either position.

Also an object of the invention is to provide an attractive, low-cost unit which may be mass produced.

Briefly stated, these objects are attained in a reversible fragrance emitting unit adapted to rest on a flat surface in either an upright or an upside down position, no fragrance being emitted in one position and fragrance being emitted in the other position, so that a switching action is effected simply by reversing the unit. The unit consists of a vented cylindrical shell closed at its upper end by a cover plate and at its lower end by a bottom wall. Disposed within the shell and secured to the cover plate is an absorbent pad. Joined to the pad is the leading end of a series of interhinged absorbent elements in an accordian formation, the trailing end of the series being joined to a weight whereby when the unit is upside down, the accordian is collapsed on the bottom wall and compressed by the overlying weight, and when the unit is reversed in position and is made upright, the weight drops to the bottom wall, thereby expanding the accordian. The pad and the elements of the accordian are impregnated with a volatile fragrance, the pad acting as a reservoir therefor, whereby in the upside down position of the unit when the accordian is collapsed, no fragrance is emitted, and when in the upright position in which the accordian is expanded to expose the elements thereof, fragrance is emitted.

BRIEF DESCRIPTION OF DRAWINGS

For a better understanding of the invention as well as other objects and further features thereof, reference is made to the following detailed description to be read in conjunction with the accompanying drawings, wherein:

FIG. 1 is a perspective view of a preferred embodiment of a reversible fragrance emitting unit in accordance with the invention, the unit being shown in its ON state in which it assumes an upright position;

FIG. 2 is a section taken through the unit shown in FIG. 1;

FIG. 3 is a section taken through the unit in its upside down position when it is in its OFF state;

FIG. 4 is a separate view of the weight at the end of the accordian included in the unit;

FIG. 5 shows the unit in its packaged state with a transparent cylindrical outer film surrounding the unit;

FIG. 6 shows the manner in which a label is inserted into a slot of the unit to render it inactive before the outer film is placed over the unit;

FIG. 7 is a longitudinal section taken through the unit in its inactive state in the plane indicated by line 7—7 in FIG. 5; and FIG. 8 is a transverse section taken through the unit in its inactive state in the plane indicated by line 8—8 in FIG. 5.

DESCRIPTION OF INVENTION

Referring now to FIGS. 1 and 2, it will be seen that a fragrance-emitting unit according to the invention includes a cylindrical shell 10 of uniform diameter which may be molded of synthetic plastic such as PVC or polyethylene or other material. Formed in the shell is a circumferential array of longitudinally-extending slots 11 which act to vent the shell to permit the discharge of fragrance therefrom into the atmosphere.

The unit is shown in its upright position placed on a flat table or other horizontal surface 12. The upper end of shell 10 is enclosed by a cover plate 13, while the lower end is enclosed by a bottom wall 14. Superposed on cover plate 13 and attached thereto is a disc-shaped pad 15 of felt, ceramic or other porous material. This attachment is effected mechanically or by a suitable bonding agent such as epoxy.

Joined to the edge of pad 15 is the leading end of a series of interhinged absorbent elements 16 to 20 which are circular in form and substantially match the diameter of pad 15. The interhinged elements may be formed of fairly stiff absorbent paper or similar material, and together create an accordian which can readily be expanded or collapsed.

The last element 20 in the accordian is nested within and joined to a dish-shaped impermeable weight 21 formed of synthetic plastic or other fairly heavy material. Hence when the unit is placed in its upright position, weight 21 drops by gravity to lie on bottom wall 14, as a result of which the accordian connected thereto is expanded to take the form shown in FIG. 2, where it will be seen that the interhinged elements thereof assume a zig-zag pattern, and that the surfaces of these elements are fully exposed.

When, however, the unit is reversed and placed in an upside-down position on surface 12, as shown in FIG. 3, then weight 20 drops toward cover plate 13 to collapse the accordian. Weight 20 then lies over the collapsed accordian to compress the elements thereof so that they lie below the slots 11. The porous pad 15 and the elements 16 to 20 of the accordian are all impregnated with a volatile fragrance or air freshener, so that when the unit is ON, as shown in FIG. 2, the perfume is then emitted from the exposed surfaces of the accordian elements. The emitted fragrance is discharged into the atmosphere from the unit through the slots 11 of the shell.

But when the unit is reversed as in FIG. 3, then the accordian is collapsed over the pad and is partially covered by the non-permeable weight 21 so that now the unit is effectively OFF and virtually no fragrance is emitted.

Thus, no mechanical expedients such as mechanical shutters are required to switch the unit ON and OFF, for one has merely to reverse the position of the unit to effect a switching action. The appearance of the unit, because it is in a simple cylindrical form with a uniform circumferential array of slots is attractive and is essentially the same, whether upright or upside down. Hence the unit may be placed on a table in a well appointed living room or at any other location without disturbing the decor, or giving the impression that it has a utilitarian function.

The unit may be in an inexpensive disposable form, such that when the fragrance is exhausted, the entire unit is then discarded and replaced. Or the shell may be made of relatively costly metallic material, in which case the cover plate 13 to which the pad and accordian are attached may be in a screw-in or snap-in form, so that the cover plate and shell may be retained and the pad and accordian replaced with a freshly impregnated pad and accordian simply by attaching these to the cover plate.

The function of the pad 15, which is substantially thicker than any element of the accordian and has only its outer face exposed, is that it serves as a reservoir for the fragrance. Hence when the elements of the accordian in the OFF state of the unit overlie the pad, these elements, by a wicking action, absorb fragrance from the pad and are thereby recharged. The material from which these elements are made, such as paper formed by non-woven, synthetic fibers, should therefore be a material having good wicking properties.

In packaging the unit, it is important that it be rendered inactive regardless of its position so that fragrance is not wasted. To this end, the margin of an identifying label 22 is inserted into one of slots 11 and then wrapped about shell 10 to encircle it. The inserted margin of the label acts to block movement of the weight 21 to maintain the weight at its OFF position. Then the unit with the label encircled about the shell is sealed by transparent packaging film so that the label is visible. Hence in its packaged state, the unit cannot be turned ON. When the film is thereafter unwrapped by the purchaser and the label withdrawn, the unit is then usable and can be turned ON and OFF.

As shown in FIGS. 5 and 6, one end of label 22 is inserted in a slot 11 in cylindrical shell 10 and is wrapped thereabout, after which a cylindrical transparent packaging film 23 is telescoped onto the label-wrapped shell to hold the label in place, the identifying or advertising material printed on the label then being visible through the film.

As shown in FIGS. 7 and 8, the end portion of label 22 which lies within shell 10 acts to hold the accordian in its compressed state, and thereby deactivates the unit during shipment and storage. But when the unit is in the hands of the end user, the outer film 23 is removed, and then the label is withdrawn, at which point the unit is in an active state and can be turned "on" or "off" in the manner previously described.

It is not essential that the unit have a uniform cylindrical form. Thus, it may have a truncated conical form, in which case the diameter of the accordian elements and the weight are made progressively larger to conform to the conical shell.

While there has been shown and described a preferred embodiment of a reversible on-off fragrance emitting unit in accordance with the invention, it will be appreciated that many changes and modifications may be made therein without, however, departing from the essential spirit thereof.

I claim:

1. A reversible fragrance emitting unit adapted to rest on a flat surface in either an upright position or an upside down position, the unit being automatically turned ON in one position and turned OFF in the other position, said unit comprising:

A a vented shell enclosed at one end by a flat cover and at the other end by a flat wall;

B an absorbent pad disposed within the shell and secured to said cover; and

C an accordian within the shell formed by a series of interhinged absorbent elements, the leading end of the series being joined to the pad and the trailing end to a weight whereby in one position of the unit the accordian is collapsed on the pad and compressed thereon by the weight; and in the other position, the accordian is expanded to expose the surfaces of its elements, and the weight rests on the wall, said pad and said elements being impregnated with a volatile fragrance which is emitted from the elements only when the accordian is expanded, and discharges into the atmosphere through the vented shell.

2. A unit as set forth in claim 1, wherein said shell is cylindrical in form and is vented by a circumferential array of longitudinal slots therein.

3. A unit as set forth in claim 1, wherein said pad is formed of felt.

4. A unit as set forth in claim 1, wherein said elements are formed of a material having good wicking properties.

5. A unit as set forth in claim 1, wherein said cover is removable.

6. A unit as set forth in claim 1, wherein said elements are circular in form and said weight is dish-shaped, the last element in the series being nested in the weight.

7. A unit as set forth in claim 2, wherein said unit is packaged by a transparent sealing film which surrounds an identifying label encircling the shell whose margin is inserted into the shell through a slot therein to prevent movement of the weight and thereby render the unit inactive.

* * * * *